United States Patent [19]

Krishnamurthy et al.

[11] Patent Number: 5,250,400
[45] Date of Patent: Oct. 5, 1993

[54] PHOTOGRAPHIC MATERIAL AND PROCESS COMPRISING A PYRAZOLOTRIAZOLE COUPLER

[75] Inventors: Sundaram Krishnamurthy, Penfield; Ping-Wah Tang; Stanley W. Cowan, both of Rochester, all of N.Y.

[73] Assignee: Eastman Kodak Company, Rochester, N.Y.

[21] Appl. No.: 841,461

[22] Filed: Feb. 26, 1992

[51] Int. Cl.$^5$ ............................................. G03C 7/38
[52] U.S. Cl. ................................... 430/386; 430/387; 430/558
[58] Field of Search .................. 430/558, 386, 387

[56] References Cited

U.S. PATENT DOCUMENTS

| | | | |
|---|---|---|---|
| 4,286,053 | 8/1981 | Ishikawa et al. | 430/557 |
| 4,540,654 | 9/1985 | Sato et al. | 430/381 |
| 4,753,870 | 6/1988 | Takada et al. | 430/516 |
| 4,777,123 | 10/1988 | Yamada et al. | 430/505 |
| 4,849,328 | 7/1989 | Hoke et al. | 430/553 |
| 4,912,027 | 3/1990 | Nishijima et al. | 430/551 |
| 4,916,051 | 4/1990 | Tachibana et al. | 430/558 |
| 4,923,791 | 5/1990 | Merkel et al. | 430/553 |
| 4,968,594 | 11/1990 | Shimazaki et al. | 430/549 |

FOREIGN PATENT DOCUMENTS

| | | |
|---|---|---|
| 0143570 | 6/1985 | European Pat. Off. ............ 430/558 |
| 240568 | 10/1987 | European Pat. Off. . |
| 349331 | 1/1990 | European Pat. Off. . |
| 381183 | 8/1990 | European Pat. Off. . |

*Primary Examiner*—Lee C. Wright
*Attorney, Agent, or Firm*—Wegner, Cantor, Mueller & Player

[57] ABSTRACT

Novel pyrazolotriazole couplers containing a ballast group of formula (I):

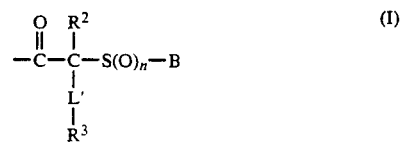

are useful in photographic materials and processes. The couplers exhibit increased coupling activity, and provide formation of dyes having improved maximum magenta image dye density, contrast, and development speed when employed in color photographic materials and processes.

14 Claims, No Drawings

PHOTOGRAPHIC MATERIAL AND PROCESS COMPRISING A PYRAZOLOTRIAZOLE COUPLER

This invention relates to novel pyrazolotriazole dye-forming couplers and to photographic silver halide materials and processes using such couplers.

Color images are customarily obtained in the photographic art by reaction between an oxidation product of a silver halide developing agent and a dye-forming coupler. Pyrazolone couplers are useful for forming magenta dye images; however, pyrazoloazole couplers, particularly pyrazolotriazole couplers, represent another class of couplers for this purpose. Examples of pyrazolotriazole couplers are described in, for example, U.S. Pat. Nos. 4,443,536; 1, 247,493; 1,252,418; and 1,398,979; and 4,665,015; 4,514,490; 4,540,654; 4,590,153; 4,822,730 and European Patent 177765. One class of pyrazolotriazole couplers includes 1H-pyrazolo[1,5-b][1,2,4] triazole couplers, such as described in European Patent 177765.

While such magenta dye-forming couplers are useful in photographic silver halide materials and processes, many of such couplers do not have sufficient coupler reactivity.

The present invention provides novel pyrazolotriazole couplers exhibiting increased coupler reactivity. The couplers contain a ballast group of formula (I):

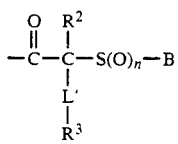
(I)

wherein: n is 0, 1 or 2;

$R^2$ represents hydrogen or a substituent;

B represents hydrogen or a substituent;

L' is selected from the group consisting of O, S, Se, Te, $Si(R^5)_2$, $NR^5$, $PR^5$, $P(O)(R^5)_2$ and $NR^5SO_2$, wherein $R^5$ represents hydrogen, alkyl or aryl; and $R^3$ represents a substituent.

Additionally, it has been found that pyrazolotriazole couplers containing the ballast of formula (I) enable the formation of dyes which exhibit improved maximum magenta image dye density ($D_{max}$), contrast, and development speed when employed in color photographic materials and processes.

An embodiment of the invention is a photographic element comprising a support bearing at least one photographic silver halide emulsion layer and a dye-forming pyrazolotriazole coupler wherein the dye-forming coupler contains a ballast of formula (I).

In a preferred embodiment, the couplers contain a ballast group of formula (Ia):

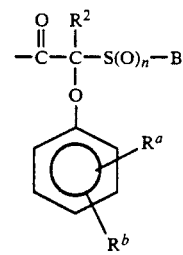
(Ia)

wherein: n, $R^2$ and B are as previously defined; and $R^a$ and $R^b$ are independently hydrogen or a substituent.

A typical coupler as described is represented by the formula (II):

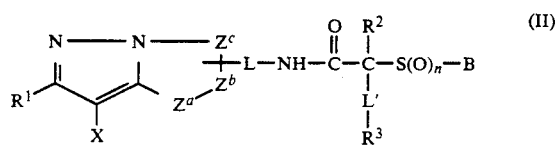
(II)

and a preferred coupler containing a ballast group of formula (Ia) is represented by formula (IIa):

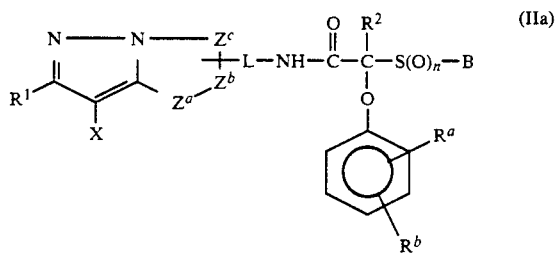
(IIa)

wherein: n, $R^2$, $R^3$, B, L', $R^a$ and $R^b$ are as previously defined;

$R^1$ represents H or a substituent;

X is hydrogen or a coupling-off group known in the photographic art;

L is a divalent linking group connecting the —NH— ballast group to the pyrazoloazole ring; and $Z^a$, $Z^b$ and $Z^c$ are independently a substituted or unsubstituted methine group, =N—, =C— or —NH—, provided that one of either the $Z^a$—$Z^b$ bond or the $Z^b$—$Z^c$ bond is a double bond and the other is a single bond, and when the $Z^b$—$Z^c$ bond is a carbon-carbon double bond, it may form part of an aromatic ring, and at least one of $Z^a$, $Z^b$ and $Z^c$ represents a methine group connected to the group L.

A preferred coupler contains a 1H-pyrazolo[1,5-b][1,2,4] triazole group and is represented by the formulae (III) and (IIIa):

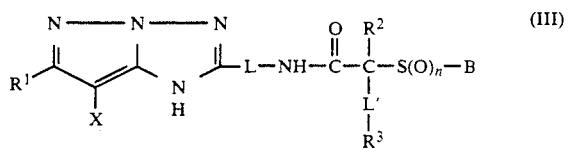
(III)

-continued
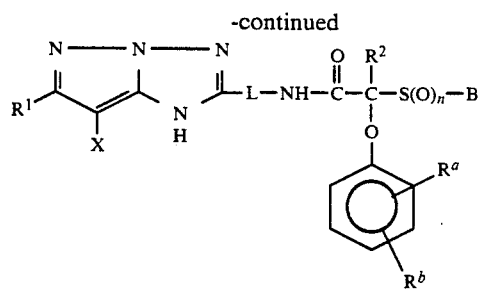
(IIIa)
wherein: n, $R^1$, $R^2$, $R^3$, B, L', $R^a$, $R^b$, X and L are as previously defined.
Illustrative examples of useful couplers as described are as follows:
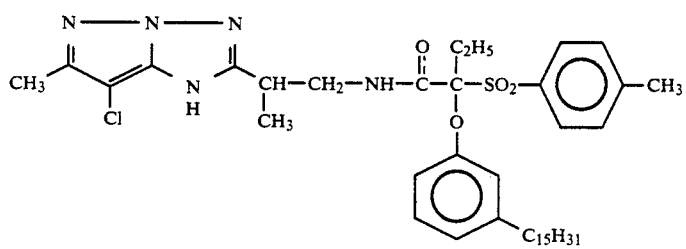
M-1
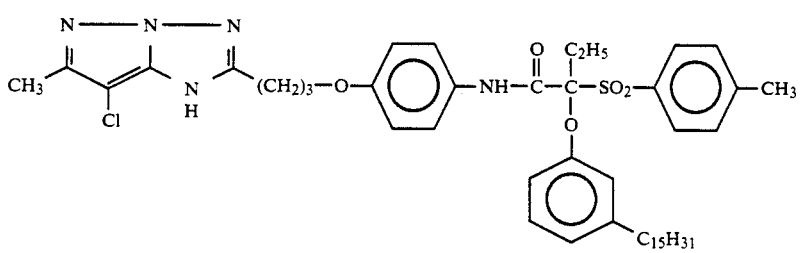
M-2
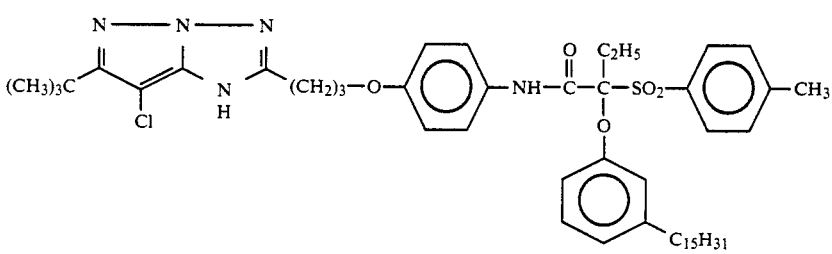
M-3
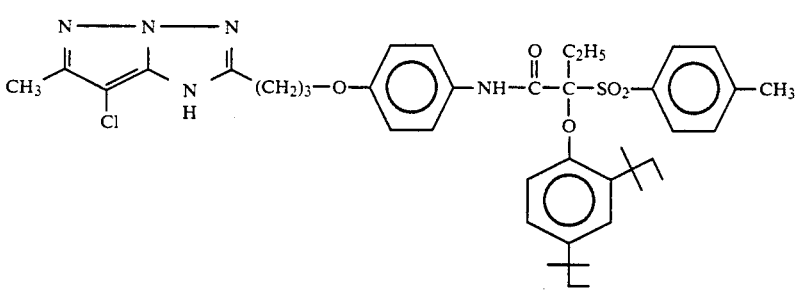
M-4
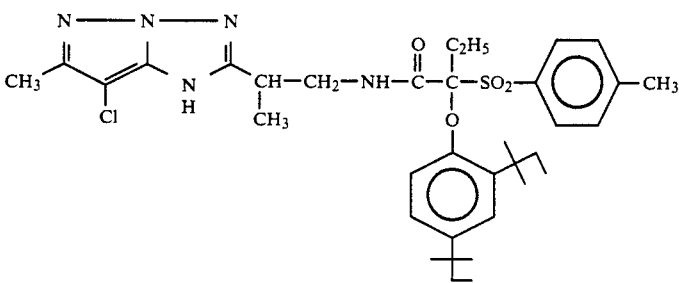
M-5

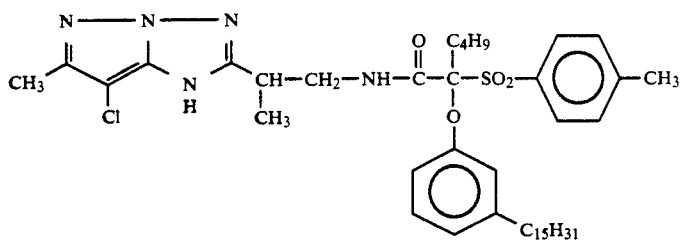
M-6
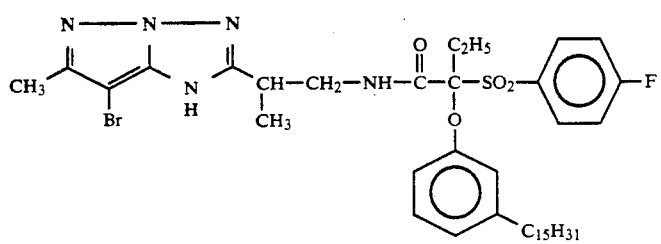
M-7
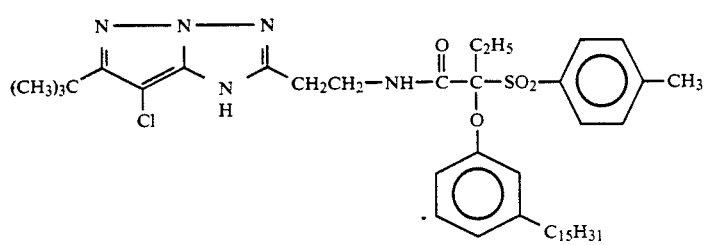
M-8
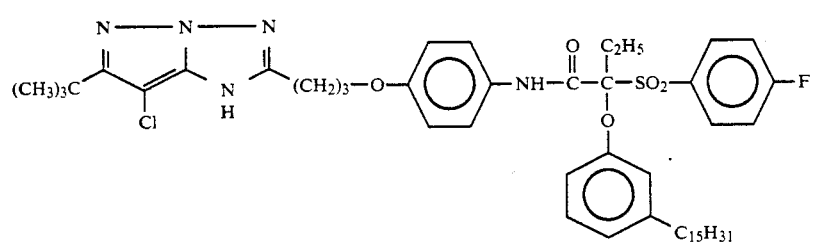
M-9
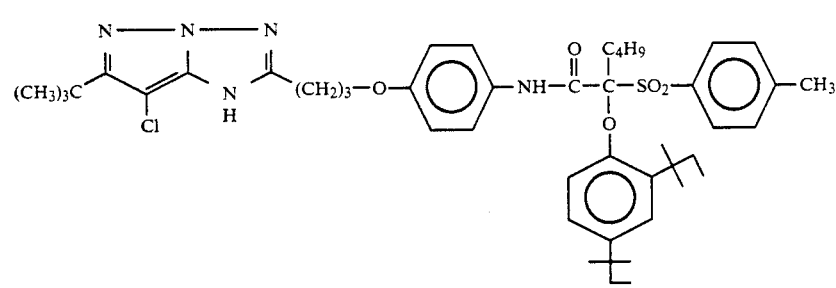
M-10
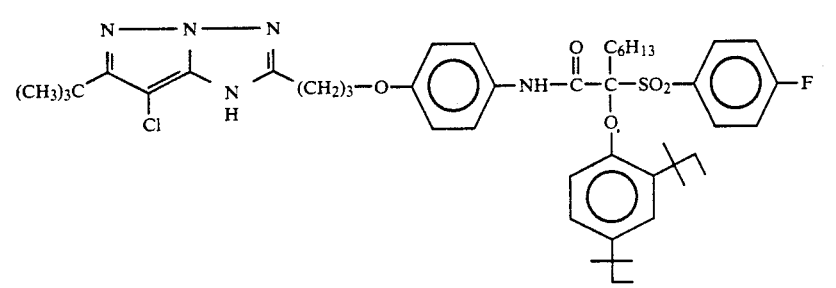
M-11

-continued

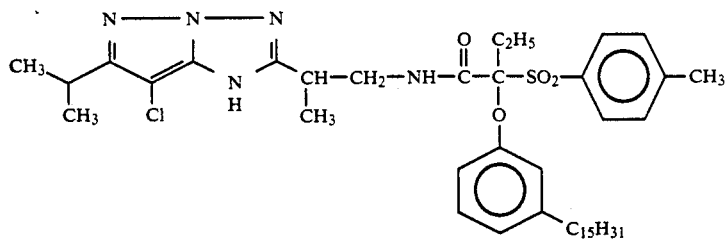
M-12

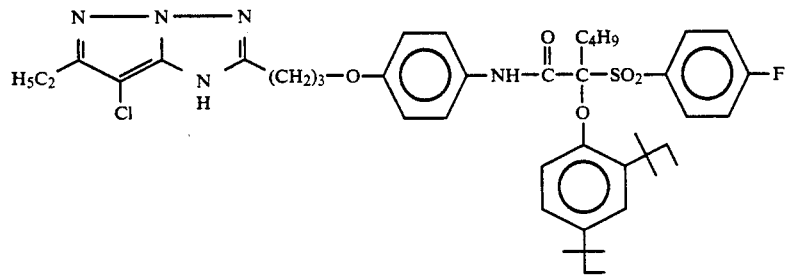
M-13

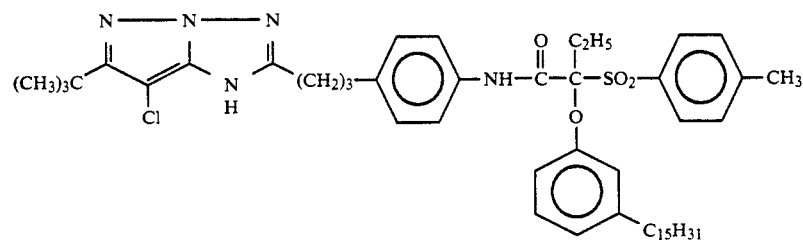
M-14

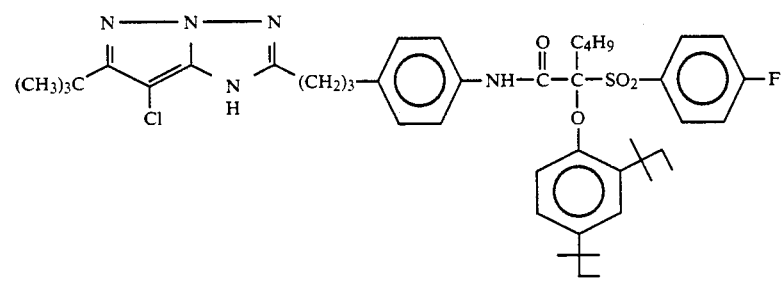
M-15

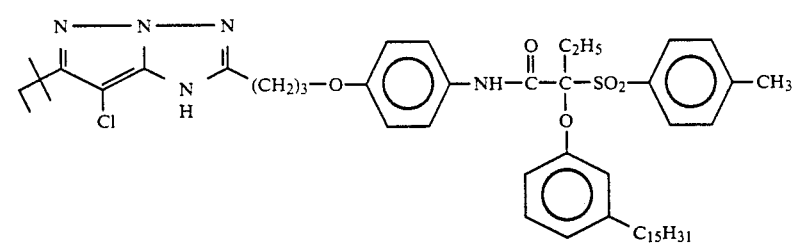
M-16

In the above formulae, n represents 0, 1 or 2. In a preferred embodiment, n is 1 or 2.

$R^1$ is hydrogen or a substituent group known in the art which typically promotes solubility, diffusion resistance or dye hue or dye stability of the dye formed upon reaction of the coupler with the oxidized color developing agent.

Examples of substituent groups for $R^1$ include: an alkyl group which may be straight or branched, and which may be substituted, such as methyl, ethyl, n-propyl, n-butyl, t-butyl, trifluoromethyl, tridecyl or 3-(2,4-di-t-amylphenoxy) propyl; an alkoxy group which may be substituted, such as methoxy or ethoxy; an alkylthio group which may be substituted, such as methylthio or octylthio; an aryl group, an aryloxy group or an arylthio group, each of which may be substituted, such as phenyl, 4-t-butylphenyl, 2,4,6-trimethylphenyl, phenoxy, 2-methylphenoxy, phenylthio or 2-butoxy-5-t-octylphenylthio; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; cyano; an acyloxy group which may be substituted, such as acetoxy or hexadecanoyloxy; a carbamoyloxy group which may be substituted, such as N-phenylcarbamoyloxy or N-ethylcarbamoyloxy; a silyloxy group which may be substituted, such as trimethylsilyloxy; a sulfonyloxy group which may be substituted, such as dodecylsulfonyloxy; an acylamino group which may be substituted, such as acetamido or benzamido; an anilino group which may be substituted, such as phenylanilino or 2-chloroanilino; an ureido group which may be substituted, such as phenylureido or methylureido; an imido group which may be substituted, such as N-succinimido or 3-benzylhydantoinyl; a sulfamoylamino group which may be substituted, such as N,N-dipropylsulfamoylamino or N-methyl-N-decylsulfamoylamino.

Additional examples of substituent groups for $R^1$ include: a carbamoylamino group which may be substituted, such as N-butylcarbamoylamino or N,N-dimethylcarbamoylamino; an alkoxycarbonylamino group which may be substituted, such as methoxycarbonylamino or tetradecyloxycarbonylamino; an aryloxycarbonylamino group which may be substituted, such as phenoxycaronylamino or 2,4-di-t-butylphenoxycarbonylamino; a sulfonamido group which may be substituted, such as methanesulfonamido or hexadecanesulfonamido; a carbamoyl group which may be substituted, such as N-ethylcarbamoyl or N,N-dibutylcarbamoyl; an acyl group which may be substituted, such as acetyl or (2,4-di-t-amylphenoxy)acetyl; a sulfamoyl group which may be substituted such as N-ethylsulfamoyl or N,N-dipropylsulfamoyl; a sulfonyl group which may be substituted, such as methanesulfonyl or octanesulfonyl; a sulfinyl group which may be substituted, such as octanesulfinyl or dodecylsulfinyl; an alkoxycarbonyl group which may be substituted, such as methoxycarbonyl or butyloxycarbonyl; an aryloxycarbonyl group which may be substituted, such as phenyloxycarbonyl or 3-pentadecyloxycarbonyl; an alkenyl group carbon atoms which may be substituted; a carboxyl group which may be substituted; a sulfo group which may be substituted; hydroxyl; an amino group which may be substituted; or a carbonamido group which may be substituted.

Substituents for the above substituted $R^1$ groups include halogen, an alkyl group, an aryl group, an aryloxy group, a heterocyclic or a heterocyclic oxy group, cyano, an alkoxy group, an acyloxy group, a carbamoyloxy group, a silyloxy group, a sulfonyloxy group, an acylamino group, an anilino group, a ureido group, an imido group, a sulfonylamino group, a carbamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group, an alkenyl group, a carboxyl group, a sulfo group, hydroxyl, an amino group or a carbonamido group.

Generally, the above groups and substituents thereof which contain an alkyl group may include an alkyl group having 1 to 16 carbon atoms. The above groups and substituents thereof which contain an aryl group may include an aryl group having 6 to 8 carbon atoms, and the above groups and substituents which contain an alkenyl group may include an alkenyl group having 2 to 6 carbon atoms.

Preferably, $R^1$ represents hydrogen, an alkyl group, an aryl group, a carbonamido group, a sulfonamido group, a sulfone group, a thio group, a sulfoxide group, a ureido group or a multicyclic group.

The pyrazolotriazole contains in the coupling position, represented by X in formulae (II) and (III), hydrogen or a coupling-off group also known as a leaving group.

Coupling-off groups are known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction, and the like. Representative classes of coupling-off groups include halogen, particularly chlorine, bromine, or fluorine, alkoxy, aryloxy, heterocyclyloxy, heterocyclic, such as hydantoin and pyrazolo groups, sulfonyloxy, acyloxy, carbonamido, imido, acyl, heterocyclylimido, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,34,766; and in U.K. patents and published application numbers 1,466,728; 1,531,927; 1,533,039; 2,006,755A and 2,017,704A; the disclosures of which are incorporated herein by reference.

Examples of specific coupling-off groups are

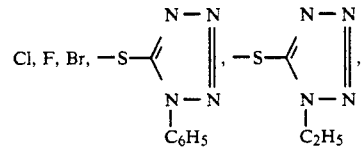

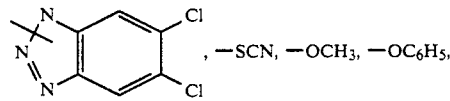

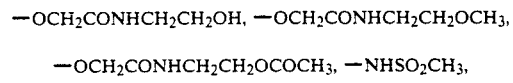

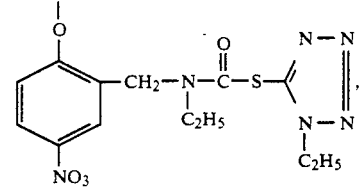

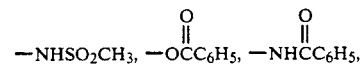

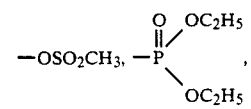

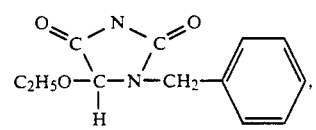

-continued

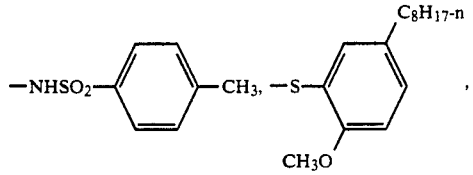

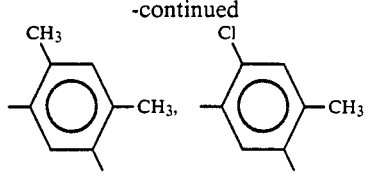

Preferably, R and R' are independently hydrogen or lower alkyl.

Preferred linking groups L include alkylene, alkylphenylene and alkoxyphenylene. Other linking groups L would be evident to one of ordinary skill in the art.

Generally, a ballast group is an organic radical of such size and configuration as to confer on the coupler molecule sufficient bulk to render the coupler substantially non-diffusible from the layer in which it is coated in a photographic element. Thus, the combination of groups $R^2$, B, L' and $R^3$ from formula (I), and the combination of groups $R^2$, B, $R^a$ and $R^b$ from formula (Ia), as well as linking group L, are chosen to meet this criteria as can be determined by one skilled in the art.

Pyrazolotriazole couplers as described can be used in ways and for purposes that pyrazolotriazole couplers have been used in the photographic art.

Pyrazolotriazole couplers as described are prepared by general methods of snythesis described in the art, such as in U.S. Pat. No. 4,540,654.

A preferred synthesis scheme follows. Couplers of formula (II) containing a ballast group of formula (I) can be prepared by following the scheme illustrated for couplers of formula (IIa) containing the ballast group of formula (Ia).

Preferably, X is H or halogen, and more preferably, H or Cl.

$R^2$, $R^a$, $R^b$ and B, which may be the same or different, each represents hydrogen or a substituent. In more detail, $R^2$, $R^a$, $R^b$ and B each represents hydrogen, halogen or an aliphatic residue including a straight or branched alkyl or alkenyl or alkynyl group, a heterocycle, an aralkyl group, a cycloalkyl group or a cycloalkenyl group. The aliphatic residue may be substituted with a substituent bonded through an oxygen atom, a nitrogen atom, a sulfur atom or a carbonyl group, a hydroxy group, an amino group, a nitro group, a carboxy group, an amido group, cyano or halogen.

$R^3$ represents a substituent as defined for $R^2$.

The L group links the —NH—ballast group to the pyrazolotriazole core. Suitable L groups include the following:

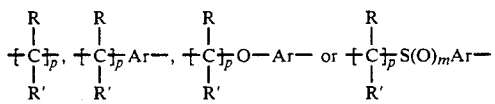

wherein: p is an integer of 1-6; m is 0, 1 or 2; R and R', which may be the same or different, each represents a hydrogen atom or a substituent; and Ar represents a substituted or unsubstituted phenylene group (for example, a 1,4-phenylene group, a 1,3-phenylene group, etc. Representative Ar group include the following:

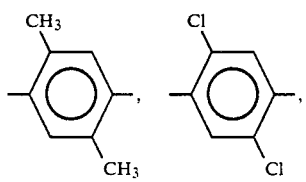

Scheme I

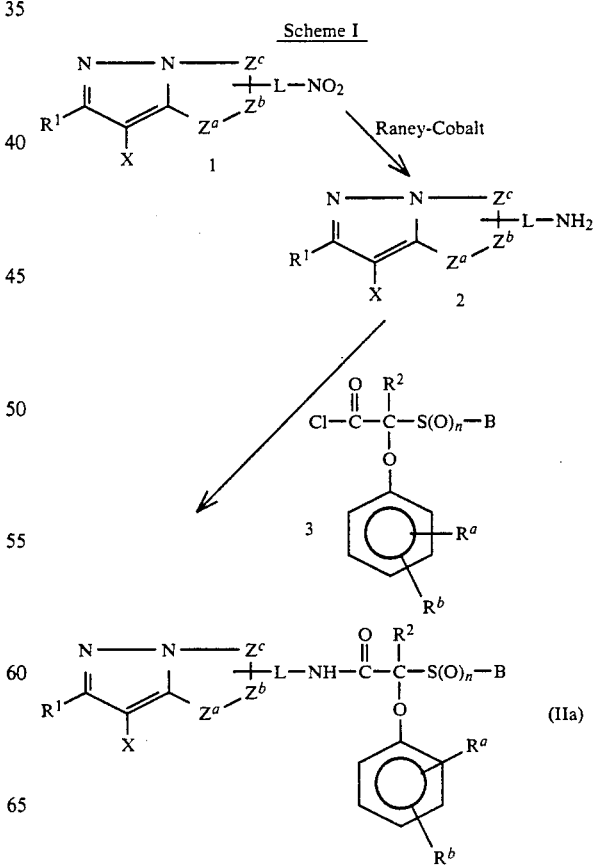

Scheme II-Preparation of ballast acid chloride
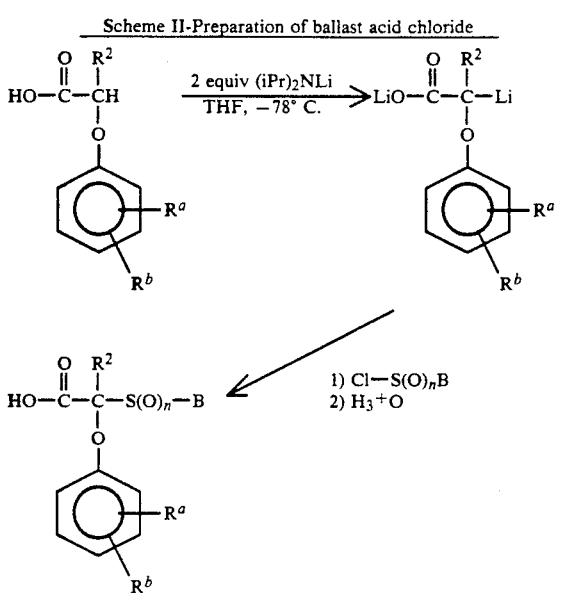
-continued
Scheme II-Preparation of ballast acid chloride
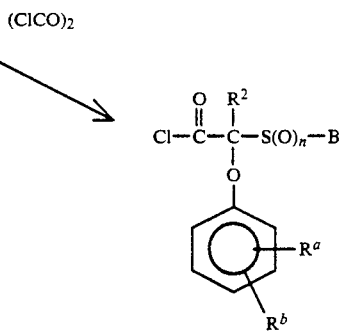
SYNTHESIS EXAMPLE—COUPLER M-3
An example of synthesis of a coupler as described is as follows:
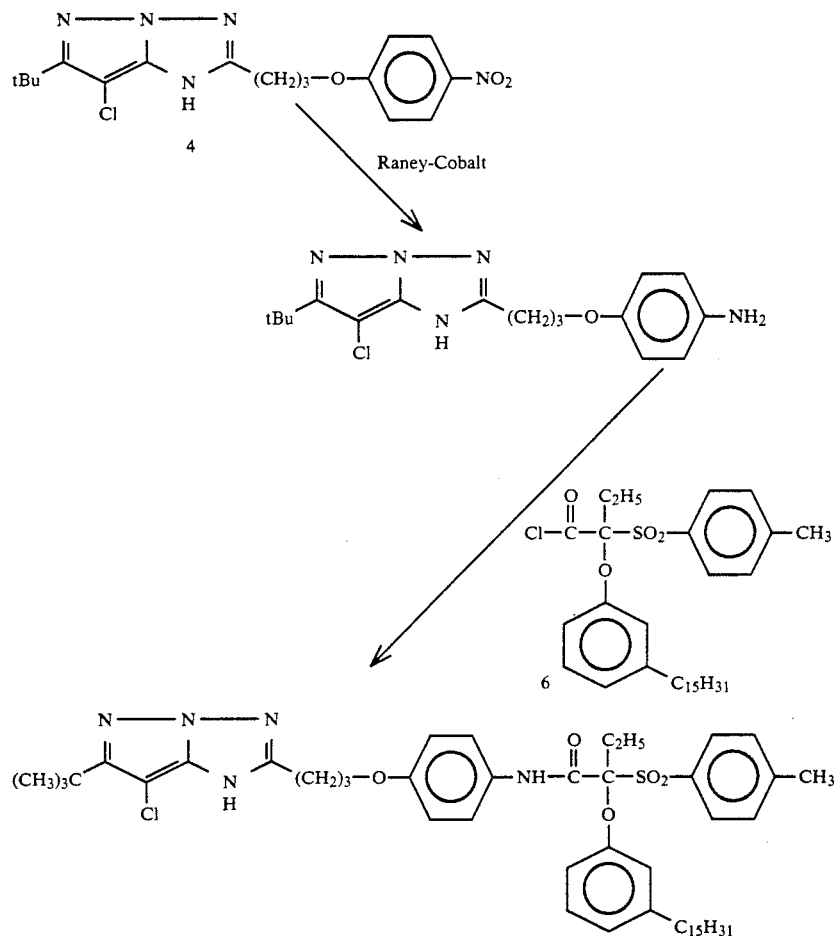
Coupler M-3
The couplers according to this invention can be prepared by following the general Scheme I as illustrated for Coupler M-3.

PREPARATION OF BALLAST ACID CHLORIDE (6)

(a) Ballast Acid of (6): To a magnetically stirred 2-L,3-neck flask, fitted with two graduated addition funnels, heat dried and cooled under a stream of argon was added freshly distilled diisopropylamine (40.9 g, 404 mmol) and tetrahydrofuran (185 mL) dried over molecular sieves. The solution Was treated with n-butyllithium (2.5M in n-hexane, 161 mL, 404 mmol) at $-20°$ C. (ice-acetone bath), added dropwise over a period of 45 min. The resulting mixture was allowed to equilibrate to 0° C. After 45 minutes at 0° C., the solution was cooled to $-78°$ C., and a solution of the ballast acid (MW 390.61, 71.7 g, 184 mmol) dissolved in THF (185 mL) was added. After 30 minutes at $-78°$ C., the mixture was stirred at 0° C. for an additional period of 30 minutes. The mixture was cooled to $-78°$ C. again and a solution of p-toluenesulfonyl fluoride (67.2 g, 386 mmol) in THF (100 mL) was added. The well stirred mixture was allowed to warm to room temperature overnight. The reaction was complete (TLC, $CH_2Cl_2$:MeOH, 9:1). The reaction was quenched by pouring into cold water (about 2L) followed by acidification to reach a pH of 1. The mixture was extracted with ethyl ether, the combined organic extracts were washed with water and brine, dried ($MgSO_4$), and concentrated in vacuo. The crude product was purified by flash chromatography to furnish 41 g of the desired ballast acid as a yellow oil.

(b) Ballast Acid Chloride (6): To a well stirred solution of the ballast acid (7.25 g, 13.3 mmol) in dichloromethane, maintained at 0° C., was added oxalyl chloride (1.97 g, 14 mmol) dropwise, followed by the addition of four drops of DMF to serve as the catalyst. The reaction mixture was stirred well and allowed to equilibrate to room temperature. The reaction was complete in 1 hour (TLC after methanolysis). The solvents were removed and the residue was repeatedly (three times) treated with 25 mL of dichloromethane, followed by removal under vacuo to furnish the ballast acid chloride (6) as a gold oil.

Preparation of a Coupler of the Present Invention (M-3)

A stirred mixture of 3.40 g (9.77 mmol) of coupler amine (5) and 1.78 g (14.7 mmol) of N,N-dimethylaniline in 30 mL of dried THF was cooled to 0° C., followed by the dropwise addition of 6.79 g (11.73 mmol) of ballast acid chloride (6) dissolved in 20 mL of THF. After the addition, the cold bath was removed and the mixture was stirred for 18 hours at 20° C. This mixture was poured into a mixture of ice-water containing 2 mL of concentrated hydrochloric acid. The organic product was extracted with three 250 mL portions of ether. The combined organic extracts were washed with water and dried over anhydrous magnesium sulfate. The mixture was filtered and the filtrate was concentrated in vacuo to yield 7.06 g (83%) of a brown oil. The crude material was purified by flash chromatography on silica gel (EtOAc/Ligroin 1:2) to yield 3.70 g (43%) of a solid (Coupler M-3). HPLC: 97%. All the analytical data were consistent with the assigned structure.

Alternate methods of synthesis are also disclosed in the following applications filed concurrently with the present application, the disclosures of which are incorporated by reference: P. Tang and T. Mungal, "Process for Preparation of 1H-Pyrazolo [1,5-b][1,2,4] Triazole Couplers and Intermediate Compounds Employed in the Process", Ser. No. 07/841,484; P Tang and T. Mungal, "Process for Preparation of 1H-Pyrazolo [1,5-b][1,2,4] Triazole Compounds by Cyclization of N-(4-Substituted-Pyrazolyl)Amidoxime", Ser. No. 07/841,463; P. Tang and T. Mungal, "Process of Preparing N-(4-Chloropyrazolyl) Amidoxime", Ser. No. 07,841,462; and P. Tang, "Method of Preparing 5-Amino-3-Substituted-Pyrazole", Ser. No. 07/841,469.

The couplers of this invention can be incorporated in silver halide emulsions and the emulsions can be coated on a support to form a photographic element. Alternatively, the couplers can be incorporated in photographic elements adjacent the silver halide emulsion where, during development, the coupler will be in reactive association with development products such as oxidized color developing agent.

The photographic elements can be either single color or multicolor elements. In a multicolor element, the magenta dye-forming coupler is usually associated with a green-sensitive emulsion, although they could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler, a magenta image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. the element can contain additional layers, such as filter layers, inter-layers, overcoat layers, subbing layers, and the like.

In the following discussion of suitable materials for use in the elements of this invention, reference will be made to *Research Disclosure*. December 1978, Item 17643, published by Kenneth Mason Publications, Ltd., The Old Harbourmaster's, 8 North Street, Emsworth, Hampshire P010 7DD, ENGLAND, and *Research Disclosure*, Dec. 1989, Item 308119, the disclosures of which are incorporated herein by reference. This latter publication will be identified hereafter by the term "*Research Disclosure.*"

The silver halide emulsions employed in the elements of this invention can be composed of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al U.S. Pat. No. 4,434,226, Daubendiek et al U.S. Pat. No. 4,414,310, Wey U.S. Pat. No. 4,399,215, Solberg et al U.S. Pat. No. 4,433,048, Mignot U.S. Pat. No. 4,386,156, Evans et al U.S. Pat. No. 4,504,570, Maskasky U.S. Pat. No. 4,400,463, Wey et al U.S. Pat. No. 4,414,306, Maskasky U.S. Pat. Nos. 4,435,501 and 4,643,966 and Daubendiek et al U.S. Pat. Nos. 4,672,027 and 4,693,964. Also specifically contemplated are those silver bromoiodide grains with a higher molar proportion of iodide in the core of the grain than in the periphery of the grain, such as those described in GB 1,027,146; JA 54/48,521; U.S. Pat. Nos. 4,379,837; 4,444,877; 4,665,012; 4,686,178; 4,565,778; 4,728,602; 4,668,614; 4,636,461; Ep 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and group VIII noble metals, can be present during precipitation of the silver halide emulsion.

The emulsions can be surface-sensitive emulsions, i.e., emulsions that form latent images primarily on the surfaces of the silver halide grains, or internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized. Noble metal (e.g., gold), middle chalcogen (e.g., sulfur, selenium, or tellurium), and reduction sensitizers, employed individually or in combination, are specifically contemplated.

Typical chemical sensitizers are listed in *Research Disclosure*, Items 17643 and 308119, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and polynuclear cyanines and merocyanines), oxonols, hemioxonols, styryls, merostyryls, and streptocyanines. Illustrative spectral sensitizing dyes are disclosed in *Research Disclosure*, Items 17643 and 308119, cited above, Section IV.

Suitable vehicles for the emulsion layers and other layers of elements of this invention are described in *Research Disclosure* Items 17643 and 308119, Section IX and the publications cited therein.

In addition to the couplers described herein the elements of this invention can include additional couplers as described in *Research Disclosure*, Items 17643 and 308119, Section VII, and the publications cited therein. These additional couplers can be incorporated as described in the above *Research Disclosure* and the publications cited therein.

The photographic elements of this invention can contain brighteners (*Research Disclosure* Items 17643 and 308119 Section V), antifoggants and stabilizers (*Research Disclosure* Items 17643 and 308119 Section VI), antistain agents and image dye stabilizers (*Research Disclosure* Items 17643 and 308119 Section VII, paragraphs I and J), absorbing and scattering materials (*Research Disclosure* Items 17643 and 308119 Section VIII), hardeners (*Research Disclosure* Items 17643 and 308119 Section X), coating aids (*Research Disclosure* Items 17643 and 308119 section XI), plasticizers and lubricants (*Research Disclosure* Items 17643 and 308119 Section XII), antistatic agents (*Research Disclosure* Items 17643 and 308119 Section XIII), matting agents (*Research Disclosure* Items 17643 and 308119 Section XVI) and development modifiers (*Research Disclosure* Items 17643 and 308119 Section XXI).

The photographic elements can be coated on a variety of supports as described in *Research Disclosure* Items 17643 and 308119 Section XVII and the references described therein.

Photographic elements can be exposed to actinic radiation, typically in the visible region of the spectrum, to form a latent image as described in *Research Disclosure* Items 17643 and 308119 Section XVIII and then processed to form a visible dye image as described in *Research Disclosure* Items 17643 and 308119 Section XIX. Processing to form a visible dye image includes the step cf contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-b-(methanesulfonamido)-ethylaniline sulfate hydrate, 4-amino-3-methyl-N-ethyl-N-b-hydroxyethylaniline sulfate, 4-amino-3-b-(methanesulfonamido)ethyl-N,N-diethylaniline hydrochloride and 4-amino-N-ethyl-N-(2-methoxy-ethyl)-m-toluidine di-p-toluene sulfonic acid.

With negative-working silver halide, the processing step described above provides a negative image. The described elements can be processed in the known C-41 color process as described in, for example, the British Journal of Photography Annual Of 1982, pages 209–211 and 1988, pages 191–198 or in known processes for processing color photographic papers, such as the known RA-4 of Eastman Kodak Company. The described elements are optionally processed in the known color processes for processing color print papers, such as the processes described in the British Journal of Photography Annual of 1988, pages 198–199. To provide a positive (or reversal) image, the color development step can be preceded by development with a non-chromogenic developing agent to develop exposed silver halide, but not form dye, and then uniformly fogging the element to render unexposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

The following examples further illustrate the invention.

Dispersions of the couplers were prepared in the following manner: The quantities of each component are found in Table I. In one vessel, the coupler, stabilizer (2,2',3,3'-tetrahydro-3,3,3',3'-tetramethyl-5,5',6,6'-tetrapropoxy-1,1'-spirobi[1H-indene]), coupler solvent (tritolyl phosphate), and ethyl acetate were combined and warmed to dissolve. In a second vessel, gelatin, surfactant (Alkanol XC and Trademark of E. I. Dupont Co., U.S.A.) and water were combined and warmed to about 40° C. The two solutions were mixed together and passed three times through a Gaulin colloid mill. The ethyl acetate was removed by evaporation and the volume was readjusted with water. The comparative couplers are listed below.

TABLE I

| Dispersion No. (Coupler No.) | Grams Coupler | Grams Stabilizer | Grams Coupler Solvent | Grams Ethyl Acetate | Grams 12.5% Gelatin | Grams Alkanol XC | Grams Water |
|---|---|---|---|---|---|---|---|
| 1 - Inv. (M-1) | 0.918 | 0.459 | 1.377 | 2.754 | 19.38 | 2.33 | 11.53 |
| 2 - Comp. (C-1) | 0.710 | 0.355 | 1.065 | 2.130 | 19.38 | 2.33 | 12.78 |
| 3 - Inv. (M-2) | 1.032 | 0.516 | 1.548 | 3.096 | 19.38 | 2.33 | 10.85 |
| 4 - Comp. (C-2) | 0.824 | 0.412 | 1.236 | 2.472 | 19.38 | 2.33 | 12.01 |
| 5 - Inv. (M-1) | 1.085 | 0.543 | 1.628 | 3.255 | 19.38 | 2.33 | 10.53 |
| 6 - Comp. (C-1) | 0.876 | 0.435 | 1.314 | 2.628 | 19.38 | 2.33 | 11.78 |

C-1 Comparative Coupler 1

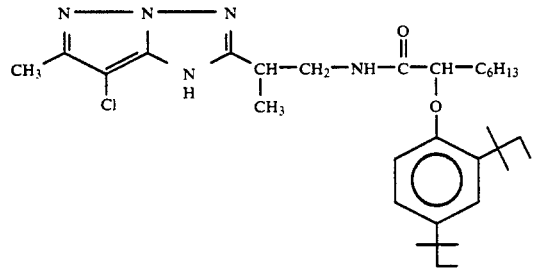

C-2 Comparative Coupler 2

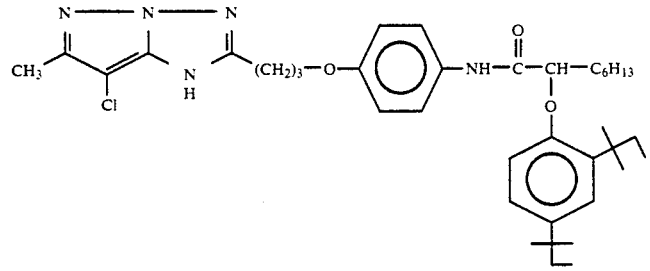

C-3 Comparative Coupler 3

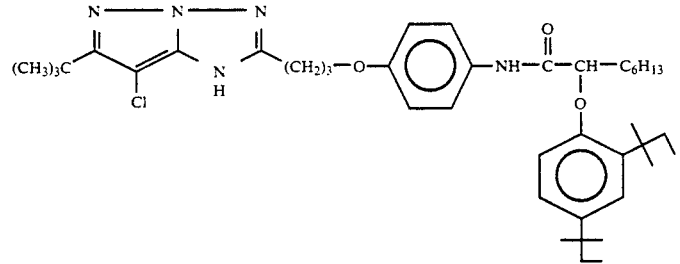

The photographic elements were prepared by coating the following layers in the order listed on a resin-coated paper support:

| 1st Layer | |
|---|---|
| Gelatin | 3.23 g/m$^2$ |
| 2nd Layer | |
| Gelatin | 1.61 g/m$^2$ |
| Coupler Dispersion (See Table II) coupler/m$^2$ | 4.3 × 10$^{-7}$ mole coupler/m$^2$ |
| Green-sensitized AgCl gelatin emulsion | 0.17 mg Ag/m$^2$ |
| 3rd Layer | |
| Gelatin | 1.33 g/m$^2$ |
| 2-(2H-benzotriazol-2-yl)-4,6-bis-(1,1-dimethylpropyl)phenol | 0.73 g/m$^2$ |
| Tinuvin 326 (U.V. absorber and trademark of Ciba-Grigg Corp., U.S.A) | 0.13 g/m$^2$ |
| 4th Layer | |
| Gelatin | 1.40 g/m$^2$ |
| Bis(vinylsulfonylmethyl)ether | 0.14 g/m$^2$ |

The photographic elements were given stepwise exposures to green light and processed as follows at 35° C.:

| Developer | 45 seconds |
|---|---|
| Bleach-Fix | 45 seconds |
| Wash (running water) | 1 minute, 30 seconds |

The developer and bleach-fix were of the following compositions:

| Developer | |
|---|---|
| Water | 700.00 mL |
| Triethanolamine | 12.41 g |
| Blankophor REU (made by Mobay Corp.) | 2.30 g |
| Lithium polyester sulfonate (30%) | 0.30 g |

-continued

| | |
|---|---|
| N,N-Diethylhydroxylamine (85%) | 5.40 g |
| Lithium sulfate | 2.70 g |
| N-{2-[(4-amino-3-methylphenyl)ethylamino]ethyl}-methanesulfonamide, sesquisulfate | 5.00 g |
| 1-Hydroxyethyl-1,1-diphosphonic acid (60%) | 0.81 g |
| Potassium carbonate, anhydrous | 21.16 g |
| Potassium chloride | 1.60 g |
| Potassium bromide | 7.00 mg |
| Water to make | 1.00 L |
| pH @ 26.7° C. adjusted to 10.4 ± 0.05 | |
| Bleach-Fix | |
| Water | 700.00 mL |
| Solution of ammonium thiosulfate (56.4%) + Ammonium sulfite (4%) | 127.40 g |
| Acetic acid (glacial) | 10.20 g |
| Solution of ammonium ferric ethylenediaminetetraacetate (44%) + ethylenediaminetetraacetic acid (3.5%) | 110.40 g |
| Water to make | 1.00 L |
| pH @ 26.7° C. adjusted to 6.7 | |

Magenta dyes were formed upon processing. The $D_{max}$ (maximum status and density to green light), contrast and relative speed (sensitivity to light) of each sample were determined by standard methods and are shown in Table II.

TABLE II

| Sample/Coupler | D-max | Constrast | Speed |
|---|---|---|---|
| 1 M-1 (Inv.) | 2.46 | 3.11 | 161 |
| 2 C-1 (Comp.) | 2.34 | 2.98 | 158 |
| 3 M-2 (Inv.) | 2.50 | 2.97 | 154 |
| 4 C-2 (Comp.) | 2.34 | 2.67 | 134 |
| 5 M-3 (Inv.) | 2.44 | 2.60 | 142 |
| 6 C-3 (Comp.) | 2.08 | 2.21 | 136 |

The data show that each coupler of the present invention yielded a higher maximum density, higher contrast and higher speed than its corresponding comparison coupler.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and a dye-forming pyrazolotriazole-based coupler, wherein the dye-forming coupler contains a ballast group of the formula (I):

$$-\overset{O}{\overset{\|}{C}}-\overset{R^2}{\underset{\underset{R^3}{\overset{|}{L'}}}{\overset{|}{C}}}-S(O)_n-B \quad (I)$$

wherein:
 n is 0, 1 or 2;
 $R^2$ is hydrogen or a substituent;
 B is hydrogen or a substituent;
 L' is selected from the group consisting of O, S, Se, Te, $Si(R^5)_2$, $NR^5$, $PR^5$, $P(O)(R^5)_2$ and $NR^5SO_2$, wherein $R^5$ is hydrogen, alkyl or aryl; and
 $R^3$ is a substituent.

2. A photographic element as in claim 1, wherein the ballast group is of the formula:

$$-\overset{O}{\overset{\|}{C}}-\overset{R^2}{\overset{|}{C}}-S(O)_n-B \quad (Ia)$$

with phenoxy substituent bearing $R^a$ and $R^b$ wherein:
 n, $R^2$, and B are as previously defined; and
 $R^a$ and $R^b$ are independently hydrogen or a substituent.

3. A photographic element as in claim 2, wherein the coupler is represented by formula (IIa):

$$\text{(IIa)}$$

wherein:
 N, $R^2$, B, $R^a$ and $R^b$ are as previously defined;
 $R^1$ is H or a substituent;
 X is hydrogen or a coupling-off group;
 L is a linking group connecting the —NH—ballast group to the pyrazoloazole ring; and
 $Z^a$, $Z^b$ and $Z^c$ are independently a substituted or unsubstituted methine group, =N—, =C— or —NH—, provided that one of either the $Z^a$—$Z^b$ bond or the $Z^b$—$Z^c$ bond is a double bond and the other is a single bond, and when the $Z^b$—$Z^c$ bond and the other is a single bond, it may form part of an aromatic ring, and wherein at least one of $Z^a$, $Z^b$ and $Z^c$ represents a methine group connect with the group L.

4. A photographic element as in claim 3, wherein the coupler is represented by formula (IIIa):

$$\text{(IIIa)}$$

5. A photographic element as in claim 4, wherein L is of the formula:

$$+\overset{R}{\underset{R'}{\overset{|}{C}}}\overset{}{\underset{}{\rightarrowtail_p}},\ +\overset{R}{\underset{R'}{\overset{|}{C}}}\overset{}{\underset{}{\rightarrowtail_p}}Ar-,\ +\overset{R}{\underset{R'}{\overset{|}{C}}}\overset{}{\underset{}{\rightarrowtail_p}}O-Ar-\ \text{or}\ +\overset{R}{\underset{R'}{\overset{|}{C}}}\overset{}{\underset{}{\rightarrowtail_p}}S(O)_m Ar-$$

wherein p is an integer of 1 to 6; m is 0, 1 or 2; R and R' are independently hydrogen or a substituent; and Ar is a substituted or unsubstituted phenylene group.

6. A photographic element as in claim 1, wherein the coupler is represented by formula (II):

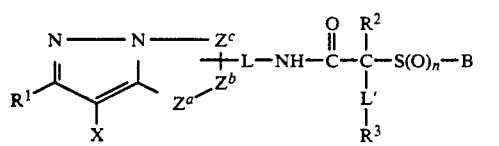

wherein:
n, $R^2$, B, L' and $R^3$ are as previously defined;
$R^1$ is H or a substituent;
X is hydrogen or a coupling-off group;
L is a linking group connecting the —NH—ballast group to the pyrazoloazole ring; and
$Z^a$, $Z^b$ and $Z^c$ are independently a substituted or unsubstituted methine group, =N—, =C— or —NH—, provided that one of either the $Z^a$—$Z^b$ bond or the $Z^b$—$Z^c$ bond is a double bond and the other is a single bond, and when the $Z^b$—$Z^c$ bond is a carbon-carbon double bond, it may form part of an aromatic ring, and wherein at least one of $Z^a$, $Z^b$ and $Z^c$ represents a methine group connect with the group L.

7. A photographic element as in claim 6, wherein the coupler is represented by formula (III):

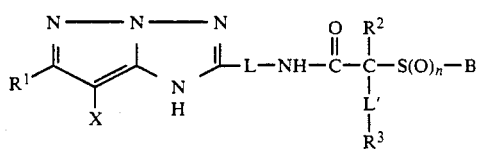

8. A photographic element as in claim 1, wherein n is 2.

9. A photographic element as in claim 5, wherein $R^a$ is H and $R^b$ is alkyl.

10. A photographic element as in claim 9, wherein n is 2, B is an aralkyl or an arylhalo group, and $R^2$ is alkyl.

11. A photographic element as in claim 10, wherein X is Cl or H.

12. A process of forming a dye image in an exposed photographic element comprising a support bearing at least one photographic silver halide emulsion layer, said process comprising developing the photographic element with a color silver halide developing agent in the presence of a color coupler of formula (I):

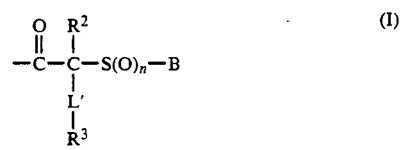

wherein:
n is 0, 1 or 2;
$R^2$ is hydrogen or a substituent;
B is hydrogen or a substituent;
L' is selected from the group consisting of O, S, Se, Te, $Si(R^5)_2$, $NR^5$, $PR^5$, $P(O)(R^5)_2$ and $NR^5SO_2$, wherein $R^5$ is hydrogen, alkyl or aryl; and
$R^3$ is a substituent.

13. A process as in claim 12, wherein the coupler is represented by formula (III):

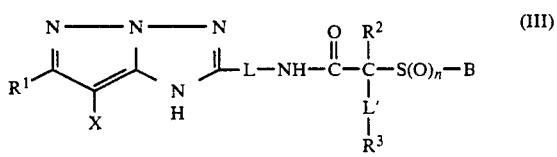

wherein:
n, $R^2$, B, L' and $R^3$ are as previously defined;
$R^1$ is H or a substituent;
X is hydrogen or a coupling-off group; and
L is a linking group connecting the —NH—ballast group to the pyrazoloazole ring.

14. A process as in claim 13, wherein the coupler is represented by formula (IIIa):

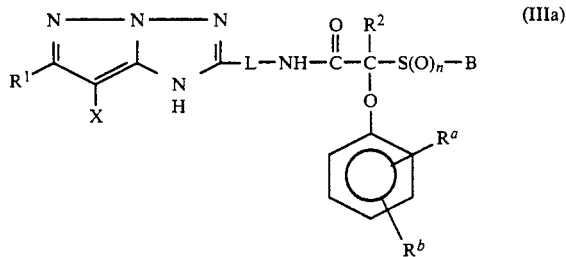

wherein:
$R^a$ and $R^b$ are independently hydrogen or a substituent.

* * * * *

UNITED STATES PATENT AND TRADEMARK OFFICE
CERTIFICATE OF CORRECTION

PATENT NO. : 5,250,400
DATED : October 5, 1993
INVENTOR(S) : S. Krishnamurthy et al It is certified that error appears in the above-indentified patent and that said Letters Patent is hereby corrected as shown below:

In Column 22, line 32, delete "N" and insert --n--.

In Column 22, line 43, delete "and the other is a single bond" and insert --is a carbon-carbon double bond--.

Signed and Sealed this

Twenty-fourth Day of May, 1994

Attest:

BRUCE LEHMAN

Attesting Officer     Commissioner of Patents and Trademarks